United States Patent [19]
Harris et al.

[11] Patent Number: 6,043,305
[45] Date of Patent: Mar. 28, 2000

[54] ALKYLENE-BRIDGED ALKYL PHOSPHONATES

[75] Inventors: Christopher John Harris, Worcester; Gary Woodward, Kidderminster; Andrew John Taylor, Bromsgrove; Jasvir Singh Manku, Oldbury, all of United Kingdom

[73] Assignee: Albright & Wilson UK Limited, West Midlands, United Kingdom

[21] Appl. No.: 08/966,438

[22] Filed: Nov. 10, 1997

[30] Foreign Application Priority Data

Nov. 13, 1996 [GB] United Kingdom .................. 9623584

[51] Int. Cl.[7] .............................. C08K 5/53; C08G 79/02; C07F 9/02
[52] U.S. Cl. .................. 524/123; 252/609; 528/400; 528/156
[58] Field of Search ................ 558/156; 524/123; 252/609; 528/400

[56] References Cited

U.S. PATENT DOCUMENTS

| | | | |
|---|---|---|---|
| 3,627,726 | 12/1971 | Krawczyk | 524/123 |
| 4,097,560 | 6/1978 | Littman et al. | 106/18.18 |
| 5,703,150 | 12/1997 | Ike et al. | 524/125 |
| 5,919,965 | 7/1999 | Gentles et al. | 558/70 |

*Primary Examiner*—Kriellion Sanders
*Attorney, Agent, or Firm*—Frishauf, Holtz, Goodman, Langer & Chick, P.C.

[57] ABSTRACT

Halogen-free, oligomeric or polymeric, alkylene-bridged alkyl phosphonates having the general formula

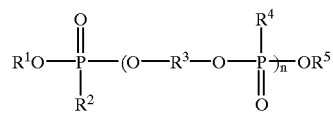

where n is a whole number of from 1 to 20;
$R^1$ and $R^5$ are each $C_1$–$C_6$ alkyl;
$R^2$ and $R^4$ are each $C_2$–$C_{10}$ alkyl and
$R^3$ is $C_2$–$C_{10}$ alkyl.

The use of such phosphonates as, or in connection with, a flame-retardant (e.g. for polyurethane foams, resins and composites, epoxy resins, phenolic resins, paints, varnishes or textiles).

23 Claims, No Drawings

ALKYLENE-BRIDGED ALKYL PHOSPHONATES

This invention relates to alkylene-bridged alkyl phosphonates, to specific phosphonates which we believe to be novel, to the use of such phosphonates as, or in connection with, flame-retardants and to articles made flame-retardant thereby.

Flame retardants are incorporated into many products on the grounds of safety in order to control the spread of fire through the product. Flame retardants can, for example, act by causing rapid extinguishing of flames, or by making the product difficult to set alight. Whilst flame retardants have conventionally been used to treat fabrics, soft furnishings etc. and have been incorporated inter alia into foams, paints and resins such as epoxy resins, many other applications are now being actively pursued, especially within the electronic, automotive, aerospace and construction industries.

Polyurethane foams are widely used for seating components of all kinds, especially seating components for automobiles. The foams are not inherently flame-retardant (indeed, the products of combustion of many polyurethane foams are highly toxic) and therefore some flame-retardant ingredient is required.

Many of the flame-retardants conventionally used in connection with polyurethane foam seating components have been found to have a tendency to migrate and/or volatilise from the foams with age. This tendency is particularly disadvantageous in the case of polyurethane foam components of automobile seating, where the migration and/or volatilisation of the flame-retardant leads to "fogging" of glass surfaces such as windows and instrument panels.

Furthermore, the use of halogen-containing phosphates as flame-retardants is regarded as undesirable on environmental grounds.

We have found that certain halogen-free oligomeric or polymeric alkylene-bridged alkyl phosphonates confer acceptable flame-retardant properties on, inter alia, polyurethane foams. These phosphonates, moreover, have been shown to minimise "fogging" when the foams are used as automobile seating components.

Accordingly, the present invention provides a halogen-free oligomeric or polymeric alkylene-bridged alkyl phosphonate having the general formula (I):

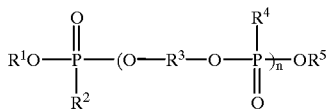

in which:
n is a whole number of from 1 to 20;
$R^1$ and $R^5$ (which may be the same or different) are each alkyl groups having from 1 to 6 carbon atoms;
$R^2$ and $R^4$ (which may be the same or different) are each alkyl groups having from 2 to 10 carbon atoms; and
$R^3$ is an alkyl group having from 2 to 10 carbon atoms which acts as an "alkylene bridging" group.

The present invention also provides, as a novel compound, a phosphonate having the general formula (I) as hereinabove described, in which:
n has an average value of 3;
$R^1$ and $R^5$ are each methyl;
$R^2$ and $R^4$ are each butyl; and
$R^3$ is hexyl.

The present invention further provides, as a novel compound, a phosphonate having the general formula (I) as hereinabove described, in which:
n has a value of 6
$R^1$ and $R^5$ are each methyl;
$R^2$ and $R^4$ are each butyl; and
$R^3$ is hexylene.

The present invention further provides, as a novel compound, a phosphonate having the general formula (I) as hereinabove described, in which:
n has an average value of 3
$R^1$ and $R^5$ are each ethyl;
$R^2$ and $R^4$ are each butyl; and
$R^3$ is hexyl.

The present invention yet further provides the use of a phosphonate having the general formula (I) as hereinabove described as a flame-retardant.

Finally, the present invention provides an article made flame-retardant by the use of a phosphonate having the general formula (I) as hereinabove described.

Referring now to phosphonates having the general formula (I), the following variations are possible within the scope of the present invention.

n may be a whole number of from 3 to 8 (eg 3);
$R^1$ and $R^5$ may each be methyl or ethyl;
$R^2$ and $R^4$ may each be alkyl groups having from 3 to 8 carbon atoms, such as from 4 to 6 carbon atoms, e.g. $R^2$ and $R^4$ may each be butyl.
$R^3$ may have from 4 to 8 carbon atoms and may, for example, be hexyl.
$R^3$ may be straight-chain or branched-chain, and may moreover contain substituents such as oxygen or nitrogen.

With reference to the use of a phosphonate according to the present invention as a flame-retardant, such use includes the provision of flame-retardant properties to foams, especially polyurethane foams. In particular, phosphonates according to the present invention find special application as flame-retardants for particles made from polyurethane foams, such as automobile seating components where "low-fogging" characteristics are desired.

Other uses of phosphonates according to the present invention include flame-retardants in, or in connection with, epoxy resins, polyurethane resins and composites, phenolic resins, paints, varnishes and textiles.

The "phosphonate" component of the oligomeric or polymeric phosphonates of the present invention is conveniently derived from phosphorous acid ($H_3PO_3$) or from alkyl or aryl derivatives thereof.

The invention will be illustrated by way of the following examples:

General procedure for preparation of oligomeric alkyl phosphonates 1) (Z+1) parts of a dialkyl phosphite are mixed and heated with Z parts of a polyhydric alcohol in the presence of 0–10 mole percent (preferably 0.1–2.0 mole percent) of a suitable transesterification catalyst, for example sodium methoxide, in the temperature range 50–200° C., (preferably 100–150° C.) to form an oligomeric H-phosphonate of unit length=Z. About 2Z units of alkyl alcohol are recovered as distillate. The actual alcohol recovered will be determined by the dialkyl phosphite used.

2) The oligomeric H-phosphonate is treated with (Z+1) parts of an unsaturated (preferably -unsaturated) hydrocarbon (e.g. an alkene or alkyne) under radical addition conditions (e.g. 140° C.; 1–2 mole % di-t-butyl peroxide as radical initiator), and optionally, in the case of a gaseous unsaturated hydrocarbon, under conditions greater than atmospheric pressure (i.e. react under pressure).
3) This yields a crude oligomeric alkyl phosphonate of high acid value, which is then treated with an appropriate method/reagent (e.g. propylene oxide) to reduce the acid value to a level appropriate for use in the application (e.g. as a flame retardant for polyurethane foams, where the acid value should not exceed 1.0 mg KOH per g.cpd.).
4) The product is vacuum-stripped to remove remaining volatiles, and the pure product recovered.

EXAMPLE 1

Preparation of an oligomeric butyl phosphonate, dimethyl ester, with n=6.

1) A reactor, configured for distillation, is charged with dimethyl phosphite (770 g; 7 moles), hexane-1,6-diol (708 g; 6 moles) and sodium methoxide (0.035 moles; 7.6 g of a 25% methanolic solution).
2) The stirred reaction mixture is heated to 90° C. at which point distillate begins to emerge. Further heating to 125° C. leads to the collection of 330 g of distillate and the formation of an oligomeric hydrogen phosphonate.
3) The apparatus is reconfigured for reflux and heated to 135° C. Butene is then introduced to the reaction mixture for a period of 10 hours, together with portions of di-t-butyl peroxide (total of 15 g; 1.5 mole %).
4) After this time, the mixture is cooled to ambient temperature to leave a crude product, which has an acid value of 8.3 mg KOH per g.cpd.
5) Propylene oxide (70 g) is added to the crude product mixture at 110° C. over a period of 3 hours, the mixture is then heated at 110° C. for a further 1 hour, then cooled to ambient temperature.
6) The reaction mixture is vacuum stripped (20 mmHg; 20–110° C.; 1 hour) to leave the product as a viscous liquid (1210 g) which has an acid value of 0.11 mg KOH per g. cpd, and a theoretical phosphorus content of 14.6%.

EXAMPLE 2

Preparation of hexylene-bridged oligomeric butyl phosphonate, diethyl ester

1) A reactor, configured for distillation, is charged with 1,6-hexanediol (354 g; 3 moles) which is then melted under inert atmosphere.
2) To this molten mixture, heated and stirred at 60° C., is added methyl acid pyrophosphate (MAPP) as a catalyst (3 drops), followed by diethyl phosphite (DEHP) (552 g; 4 moles).
3) The stirred mixture is heated slowly to 135° C., at which point a distillate begins to collect. The mixture is then heated from 135° C. to 150° C. over a period of three hours, during which time further distillate is collected. The mixture is then heated at 150° C. for a further 1 hour, during which time a nitrogen sparge is introduced into the reaction mixture. A total of 258 g of distillate (which contains principally ethanol) is collected during the heating period.
4) The mixture is cooled to 140° C. and the apparatus reconfigured for reflux. Butene is then introduced into the reaction mixture for a period of 15 hours, together with portions of di-t-butyl peroxide (total of 12 g; 2 mole % w.r.t. DEHP).
5) After this time, the mixture is cooled to ambient temperature to leave to crude product which has an acid value of 16.5 mg KOH per g.cpd.
6) The crude product mixture is heated at 110° C. Propylene oxide (60 g) is added over a period of 3 hours. The mixture is heated at 110° C. for a further 1 hour, then cooled to ambient temperature.
7) The reaction mixture is vacuum-stripped (20 mmHg; 20–110° C.; 1 hour) to leave the product as a viscous, pale yellow liquid (844 g) which has an acid value of 0.6 mg KOH per g.cpd., and a theoretical phosphorus content of 14.5%.

EXAMPLE 3

Preparation of hexylene-bridged oligomeric butyl phosphonate, dimethyl ester

1) A reactor, configured for distillation, is charged with 1,6-hexanediol (354 g; 3 moles) which is then melted under inert atmosphere.
2) To this molten mixture, heated and stirred at 60° C., is added methyl acid pyrophosphate (MAPP) as a catalyst (3 drops), followed by dimethyl phosphite (DMHP) (440 g; 4 moles).
3) The stirred mixture is heated slowly to 125° C., at which point a distillate begins to collect. The mixture is then heated from 125° C. to 150° C. over a period of three hours, during which time further distillate is collected. The mixture is then heated at 150° C. for a further 1 hour, during which time a nitrogen sparge is introduced into the reaction mixture. A total of 168 g of distillate (which contains principally methanol) is collected during the heating period.
4) The mixture is cooled to 140° C. and the apparatus reconfigured for reflux. Butene is then introduced to the reaction mixture for a period of 15 hours, together with portions of di-t-butyl peroxide (total of $^{12}$ g; 2 mole % w.r.t. DMHP).
5) After this time, the mixture is cooled to ambient temperature to leave a crude product which has an acid value of 29.6 mg KOH per g.cpd.
6) The crude product mixture is heated at 110° C. Propylene oxide (50 g) is added over a period of 3 hours. The mixture is heated at 110° C. for a further 1 hour, then cooled to ambient temperature.
7) The reaction mixture is vacuum-stripped (20 mmHg; 20–110° C.; 1 hour) to leave the product as a viscous, pale yellow liquid (823 g) which has an acid value of 1.1 mg KOH per g.cpd., and a theoretical phosphorus content of 15.0%.

EXAMPLE 4

A conventional halogenated alkyl phosphate and the product of the Example 1 (above) were each used as the flame-retardant additive for the production of a polyurethane foam. The quantities used and the results obtained are shown in Table I (below).

TABLE I

| Polyether foam formulations | | Phosphonate of Invention | Control Phosphate |
|---|---|---|---|
| Polyether Polyol (OH value = 48) | parts | 100.00 | 100.00 |
| Water | parts | 4.15 | 4.15 |
| (a) catalyst I | parts | 0.04 | 0.04 |
| (b) catalyst II | parts | 0.12 | 0.12 |
| (c) Surfactant | parts | 1.30 | 1.30 |
| Stannous Octoate | parts | 0.25 | 0.25 |
| Toluene Di-isocyanate | index | 110 | 110 |
| (d) Phosphonate of Invention | parts | 10.00 | |
| (e) Control Phosphate | parts | — | 13.00 |
| Cream Time | s | 19.00 | 20.00 |
| Rise Time | s | 105.00 | 111.00 |
| Density | kg/m$^3$ | 23.60 | 26.20 |
| Indicative Federal Motor Vehicles Safety Standard 302 Performance | | | |
| Burn Length | mm | — | — |
| Burn Time | s | — | — |
| Rating | | Self-extinguishing | Self-extinguishing |
| Indicative DIN 75201 Part B Fogging Performance | | | |
| Fogging | mg/10 mm foam | 0.45 | 1.18 |

Notes to Table I
(a) An amine catalyst comprising 70% bis(2-dimethylaminoethyl) ether and 30% dipropylene glycol, available as NIAX* A1.
(b) An amine catalyst comprising 33% diaza-bicyclo-octane and 67% dipropylene glycol, available as DABCO* 33LV.
(c) A polyether-modified polysiloxane, available as TEGOSTAB* BF2370.
(d) The product of Example 1 i.e. a hexylene-bridged oligomeric butyl phosphonate (dimethyl ester).
(e) A chlorinated alkyl phosphate, available as AMGARD* V6.
*NIAX, DABCO, TEGOSTAB AND AMGARD are Registered Trade Marks.

We claim:

1. A halogen-free alkylene-bridged alkyl phosphonate having the general formula (I):

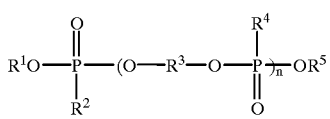

wherein:
n is a whole number of from 1 to 20;
R$^1$ and R$^5$ (which may be the same or different) are each alkyl groups having from 1 to 6 carbon atoms;
R$^2$ and R$^4$ (which may be the same or different) are each alkyl groups having from 2 to 10 carbon atoms; and
R$^3$ is an alkyl group having from 2 to 10 carbon atoms which acts as an alkylene bridging group.

2. The phosphonate of claim 1, wherein, in said formula (I), n is a whole number of from 3 to 8.

3. The phosphonate of claim 1, wherein, in said formula (I), n has an average value of 3.

4. The phosphonate of claim 1, wherein, in said formula (I), R$^1$ and R$^5$ are each methyl.

5. The phosphonate of claim 1, wherein, in said formula (I), R$^1$ and R$^5$ are each ethyl.

6. The phosphonate of claim 1, wherein, in said formula (I), R$^2$ and R$^4$ (which may be the same or different) are each alkyl groups having from 3 to 8 carbon atoms.

7. The phosphonate of claim 6, wherein, in said formula (I), R$^2$ and R$^4$ (which may be the same or different) are each alkyl groups having from 4 to 6 carbon atoms.

8. The phosphonate of claim 7, wherein, in said formula (I), R$^2$ and R$^4$ are each butyl.

9. The phosphonate of claim 1, wherein, in said formula (I), R$^3$ is an alkyl group having from 4 to 8 carbon atoms.

10. The phosphonate of claim 9, wherein, in said formula (I), R$^3$ is hexyl.

11. The phosphonate of claim 9, wherein, R$^3$ is a straight-chain alkyl group.

12. The phosphonate of claim 9, wherein, R$^3$ is a branched-chain alkyl group.

13. The phosphonate of claim 1, wherein, in said formula (I), R$^3$ includes at least one substituent.

14. The phosphonate of claim 13, wherein said at least one substituent is selected from the group consisting of oxygen and nitrogen.

15. The phosphonate of claim 1, wherein, in said formula (I):
n has an average value of 3;
R$^1$ and R$^5$ are each methyl;
R$^2$ and R$^4$ are each butyl; and
R$^3$ is hexyl.

16. The phosphonate of claim 1, wherein, in said formula (I):
n has an average value of 6;
R$^1$ and R$^5$ are each methyl;
R$^2$ and R$^4$ are each butyl; and
R$^3$ is hexylene.

17. The phosphonate of claim 1, wherein, in said formula (I):
n has an average value of 3;
R$^1$ and R$^5$ are each ethyl;
R$^2$ and R$^4$ are each butyl; and
R$^3$ is hexyl.

18. A material containing a flame-retardant amount of the phosphonate of claim 1.

19. The material of claim 18, said material comprising at least one polyurethane foam.

20. The material of claim 18, said material comprising at least one substance selected from the group consisting of epoxy resins, polyurethane resins, polyurethane composites, phenolic resins, paints, varnishes and textiles.

21. The material of claim 18, wherein said phosphonate has the general formula:

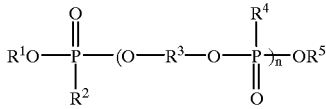

in which:
n=3;
R$^1$ and R$^5$ are each methyl or ethyl;
R$^2$ and R$^4$ are each butyl; and
R$^3$ is hexyl.

22. The phosphonate of claim 1, wherein, in said formula (I),
n has an average value of 3 or 6;
R$^1$ and R$^5$ are methyl or ethyl; and
R$^2$ and R$^4$ are butyl.

23. The phosphonate of claim 22, wherein, in said formula (I),
R$^1$ and R$^5$ are both methyl or both ethyl; and
R$^3$ contains 6 carbon atoms.

* * * * *